United States Patent [19]

Techiera

[11] Patent Number: 5,658,291
[45] Date of Patent: Aug. 19, 1997

[54] MEDIAN RIDGE REFERENCING PATELLA CUTTING SYSTEM

[75] Inventor: Richard C. Techiera, Avon, Mass.

[73] Assignee: Johnson & Johnson Medical, Inc., Arlington, Tex.

[21] Appl. No.: 537,044

[22] Filed: Sep. 29, 1995

[51] Int. Cl.$^6$ ............................................. A61B 17/56
[52] U.S. Cl. ................................. 606/80; 606/88
[58] Field of Search ......................... 606/80, 87, 88, 606/99, 102; 623/20

[56] References Cited

U.S. PATENT DOCUMENTS

| | | | |
|---|---|---|---|
| 5,129,907 | 7/1992 | Heldreth et al. | 606/80 |
| 5,129,908 | 7/1992 | Peterson | 606/88 |
| 5,222,955 | 6/1993 | Mikhail | 606/80 |
| 5,284,482 | 2/1994 | Mikhail | 606/86 |
| 5,486,177 | 1/1996 | Mumme et al. | 606/79 |
| 5,520,692 | 5/1996 | Ferrante | 606/80 |
| 5,536,271 | 7/1996 | Daly et al. | 606/80 |

Primary Examiner—Michael Buiz
Assistant Examiner—David O. Reip
Attorney, Agent, or Firm—Susan M. Schmitt

[57] ABSTRACT

A median ridge referencing system and method of use in prosthetic knee implantation surgery is provided. The median ridge referencing system comprises a patella clamp including a guide sleeve having a length and a lumen extending through the length and a referencing device comprising a stop ring and stop plug. The ring may be coupled to the guide sleeve at a plurality of locations along the length of the guide sleeve. The stop plug is removably coupled to the stop ring, and extends into lumen of the guide sleeve until it reaches the bone. The stop ring is then coupled to the guide sleeve and the stop plug is removed. A reamer is inserted into the lumen of the guide sleeve and used to ream the patella until the reamer's stop reaches the top of the stop ring. When the reamer reaches the top of the stop ring, the patella has been reamed to the proper depth for insertion of the patella prosthesis.

8 Claims, 6 Drawing Sheets

MEDIAN RIDGE REFERENCING PATELLA CUTTING SYSTEM

FIELD OF THE INVENTION

The present invention relates to a patella reaming system for sizing the reams or cuts to a patella in preparation for the implantation of the patella component of an artificial knee system.

BACKGROUND OF THE INVENTION

Patella prothesis have been used in total knee replacement surgery to insure a reproducible interaction of a patella with the femoral and tibial portions of the total knee replacement. Usually in such procedures the posterior side of the patella is prepared, sized and reamed so that the patella implant, when fixed to the patella, restores the reconstructed patella to its natural or original thickness.

Generally, during such procedure, the posterior side of the patella is exposed. The patella is then clamped so that the posterior side of the patella may be cut and then reamed. Prior to cutting and reaming the patella, a caliper is used to measure the preoperative patella height. In one procedure the patella is prepared for the patellar implant as follows. A patellar holding clamp is placed on the patella with a clamp ring on the posterior side. With the clamp on, a guide wire is inserted through the patella from a pre-marked location on the patellar posterior side through the patellar anterior side. The patella is planed with a cannulated planer through the clamp ring with the guide wire guiding the planer. A stop on the planer contacts the top of the clamp ring when a predetermined planing depth is reached. This depth is constant for each size. The patella is then reamed with a reamer inserted over the guide wire. The predetermined ream depth is determined when the reamer stop head having the same or smaller circumference as that of the cut plane, hits the planed bone. The patellar implant is then inserted into the prepared bed.

One disadvantage of this technique is the planing and reaming depth is referenced from where the clamp ring clamps the patellar bone. The system approximates the original patellar thickness based on an average thickness. Thus, although the system estimates original thickness, it does not provide adjustable cutting depths based on the variable of patellar dome height, i.e., the most prominent posterior point, typically the patellar median ridge.

In another patella implant procedure, after measuring the thickness of the patella, a depth stop plug is dropped down to contact the median ridge, i.e., the most prominent part of the patella anterior. The stop plug includes a ruler from which a measurement may be taken. The thickness of the patella and the measurement of the stop plug are used to calculate where to set the reamer stop. A reamer stop comprised of ring on the reamer is set to the scale so that the reamer will stop at the appropriate location. The final post operative height generally should correspond within plus or minus 1 mm of the original preoperative height, (unless another height is specifically desired). The reamer reams to a depth appropriate for the implant thickness. When the implant is in place, the restored height should be within 1 mm of the preoperative height.

One disadvantage of this technique is that it requires accurate measurements, e.g., of the thickness of the patellar bone and the location of the depth stop plug, and accurate calculations in order determine the depth of the ream for preparing the patella implant. Accordingly, one object of the present invention is to provide a patella referencing and reaming instrument which avoids the necessity to make specific measurements and calculations based on those measurements, in order to accurately size the reams and/or cuts in the patella.

SUMMARY OF THE INVENTION

The present invention provides a method and device for preparing a patella for a patella implant. According to a preferred embodiment of the present invention, the patella is sized, then marked, and then clamped with an appropriate sized guide sleeve for an appropriate sized reamer. A stop plug and a reamer stop ring are assembled by inserting the stop plug into the ring. The assembly is dropped over the guide sleeve until the stop plug contacts the patella bone. The ring includes spring loaded quick release levers with multiple grouped serrations matching serrations on the outer circumference of the guide sleeve. The levers are squeezed to allow the ring to slide over the sleeve and the levers are released to lock the ring on the sleeve when the stop plug reaches the bone. Thus, the ring is locked on the sleeve at a particular preset height above the bone.

Each reamer of the system contains a stop head so that when a reamer is inserted through the guide sleeve and used to ream the bone, the reamer will stop when it contacts the top of the stop ring. The reamer stop head is located at a preset height from the cutting end of the reamer so that when the stop head hits the top of the stop ring, the reamer will have reamed the bone to a preset depth in the bone. The reamer stop head predetermined depth is set so that the ream depth is matched to the thickness and/or depth of the patella implant, thus, controlling the depth of the reaming. If more than one reaming instrument is used, e.g., in a multiple step reaming procedure where different types of cuts are made in the bone, each of the reaming instruments will have a reamer stop head set according to the preset desired reaming depth for that instrument. Alternatively multiple cutting instruments may be used, e.g., a system which uses a planer and then a reamer to prepare the tibial bone. In such case, each cutting instrument would have a stop head located at a predetermined cut depth corresponding to the implant depth and shape.

DETAILED DESCRIPTION OF THE DRAWINGS

DETAILED DESCRIPTION OF THE INVENTION

Referring now to FIGS. 1–8, a median ridge referencing patella instrument system of the present invention is illustrated. The system includes a clamp 10 including a pedestal 11 with pins 12 to be secured to the anterior portion 15 of the patella 50. The clamp 10 further includes a guide sleeve 16 having bony teeth 17 to be positioned on the posterior side 18 of the patella 50. The guide sleeve 16 further comprises serrations 35 longitudinally spaced from each other in 1 mm increments from tip to tip.

Figure 2:
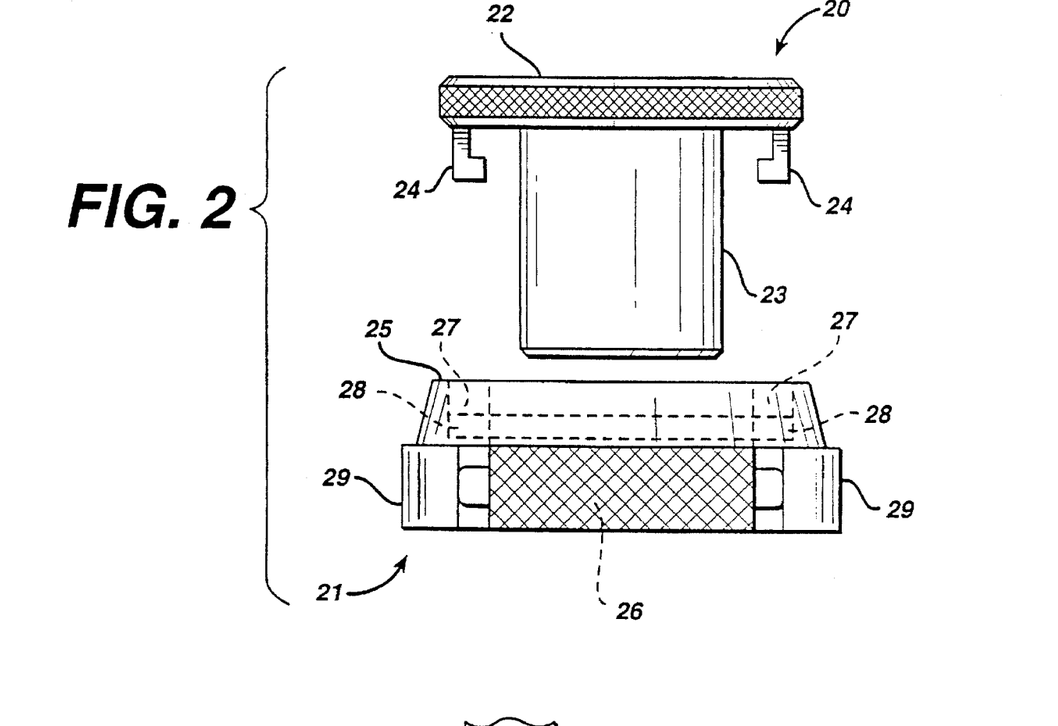
FIG. 2 illustrates an exploded side view of a depth stop ring and depth stop plug of the median ridge referencing system of the present invention.
Figure 3:
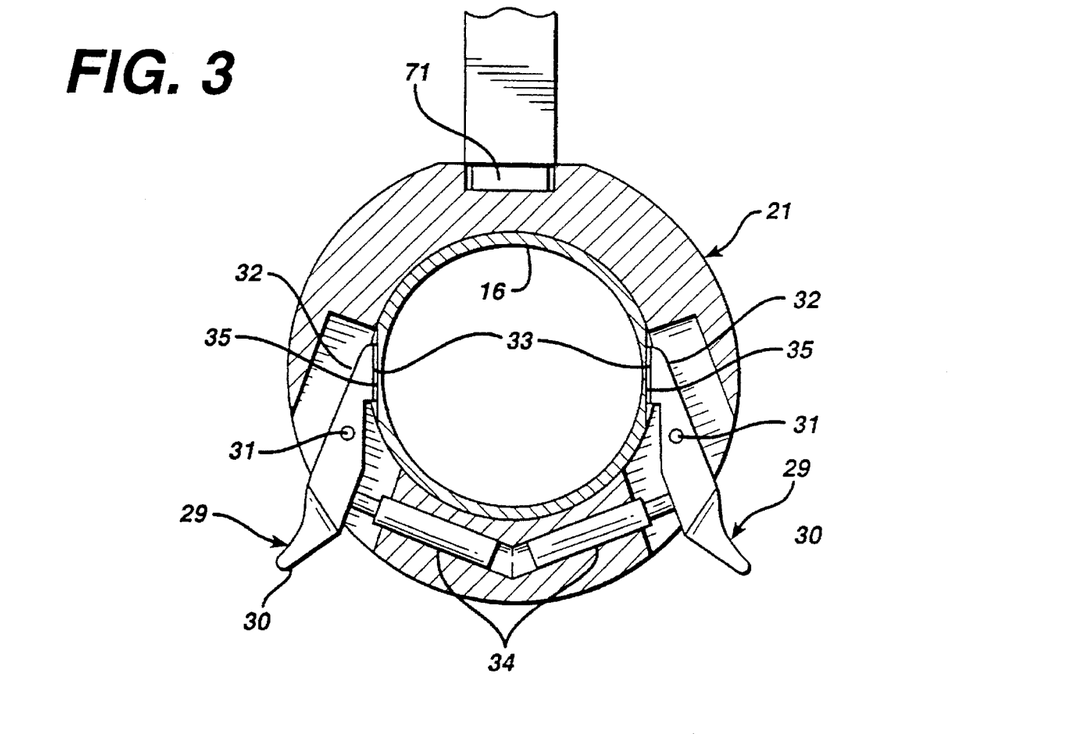
FIG. 3 illustrates a top cross-sectional view of the depth stop ring of FIG. 2.

FIGS. 2 and 3 illustrate a depth stop plug 20 and a depth stop ring 21. The depth stop plug 20 includes a head 22, a downwardly extending cylinder 23, and pins 24 extending downward from the outer circumference of the head 22. The depth stop ring 21 comprises a circumferential top portion 25 having an opening 26 for receiving a cylindrical portion 23 of the depth stop plug 20. The depth stop ring 21 further comprises two holes 27 for receiving the pins 24 of the depth stop plug 20. Groove 28 is formed in the inner circumference of the depth stop ring 21, for locking the depth stop plug 20 into place after inserting the pins 24 of the plug 20 into the holes 27 of the depth stop ring 21 and rotating the plug 20 so that pins are locked in groove 28.

The depth stop ring 21 also comprises a pair of quick release height locking levers 29. The levers 29 include tab portions 30 which extend out of the outer circumference of the depth stop ring 21. The levers 29 are coupled to the depth stop ring 21 by way of pins 31 about which the levers are permitted to pivot. The end of the levers 32 include serrations 33 arranged to interact with the serrations 35 located on the outer circumference of the guide sleeve 16. The levers 29 are biased by a ball plunger spring 34 in a direction in which the serrations 33 of the levers 29 engage with serrations 35 of the guide sleeve 16. The tab portions 30 may be depressed to release the levers 29 from engagement with the guide sleeve 16. When the tabs 30 are released, the spring 34 causes the lever 29 and the serrations 33 of the levers 29 to engage with the serrations 35 of the guide sleeve 16.

Figure 6:
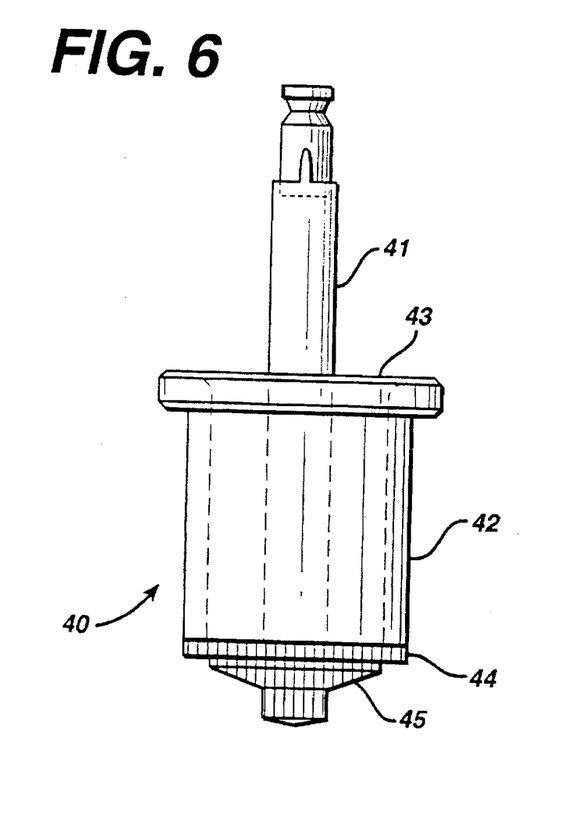
FIG. 6 illustrates a single step reamer of the present invention.

FIG. 6 illustrates a reamer 40 of the system of the present invention. The reamer includes a shaft 41 coupled to a stop head 43 coupled to a base or guiding portion 42. The guiding portion 42 has a cutting portion 45 located on a cutting end 44 of the guiding portion 42.

Figure 1:
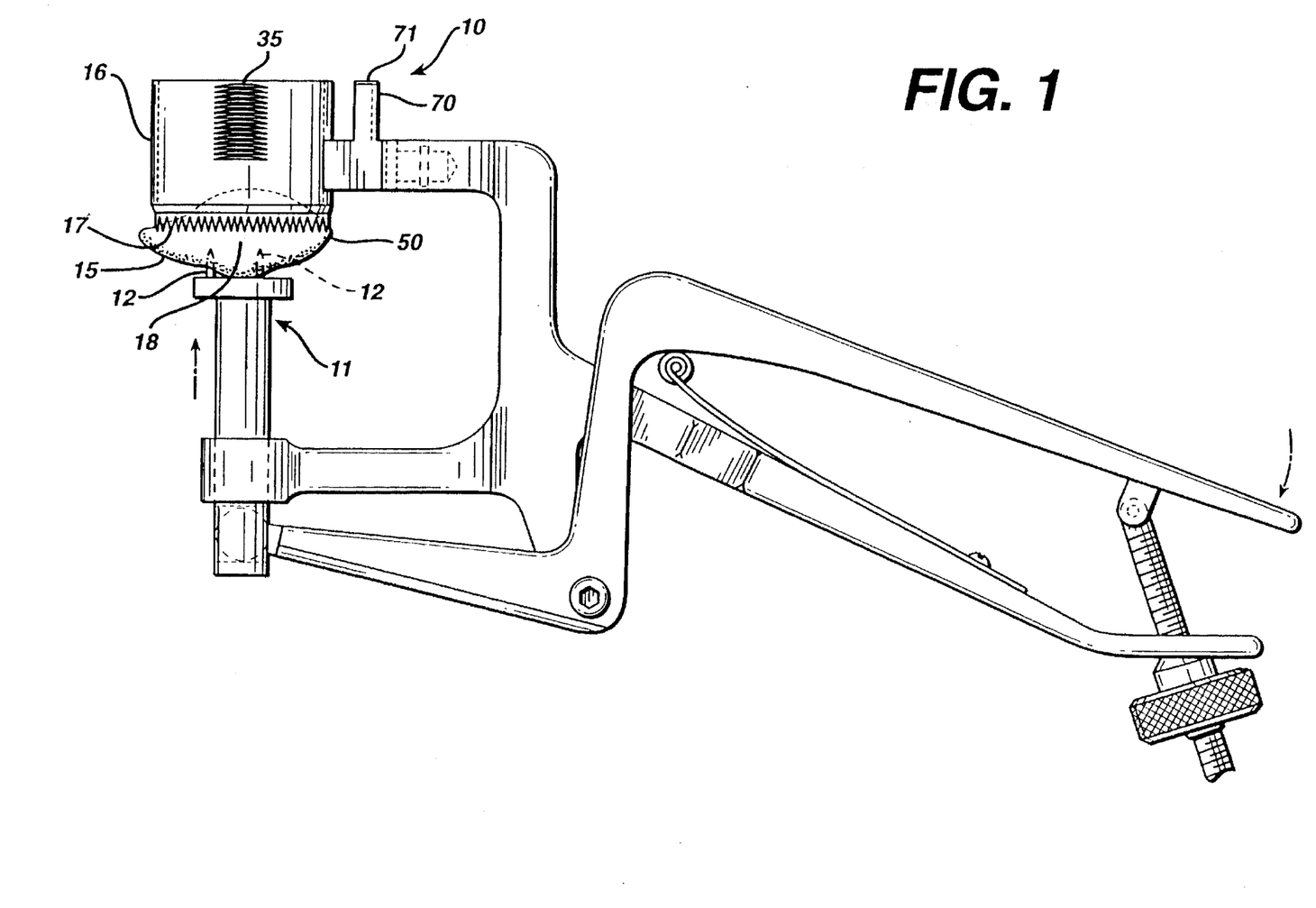
FIG. 1 illustrates a side cross-sectional view of a clamp with a guide sleeve clamped onto a patella to be resurfaced.
Figure 4:
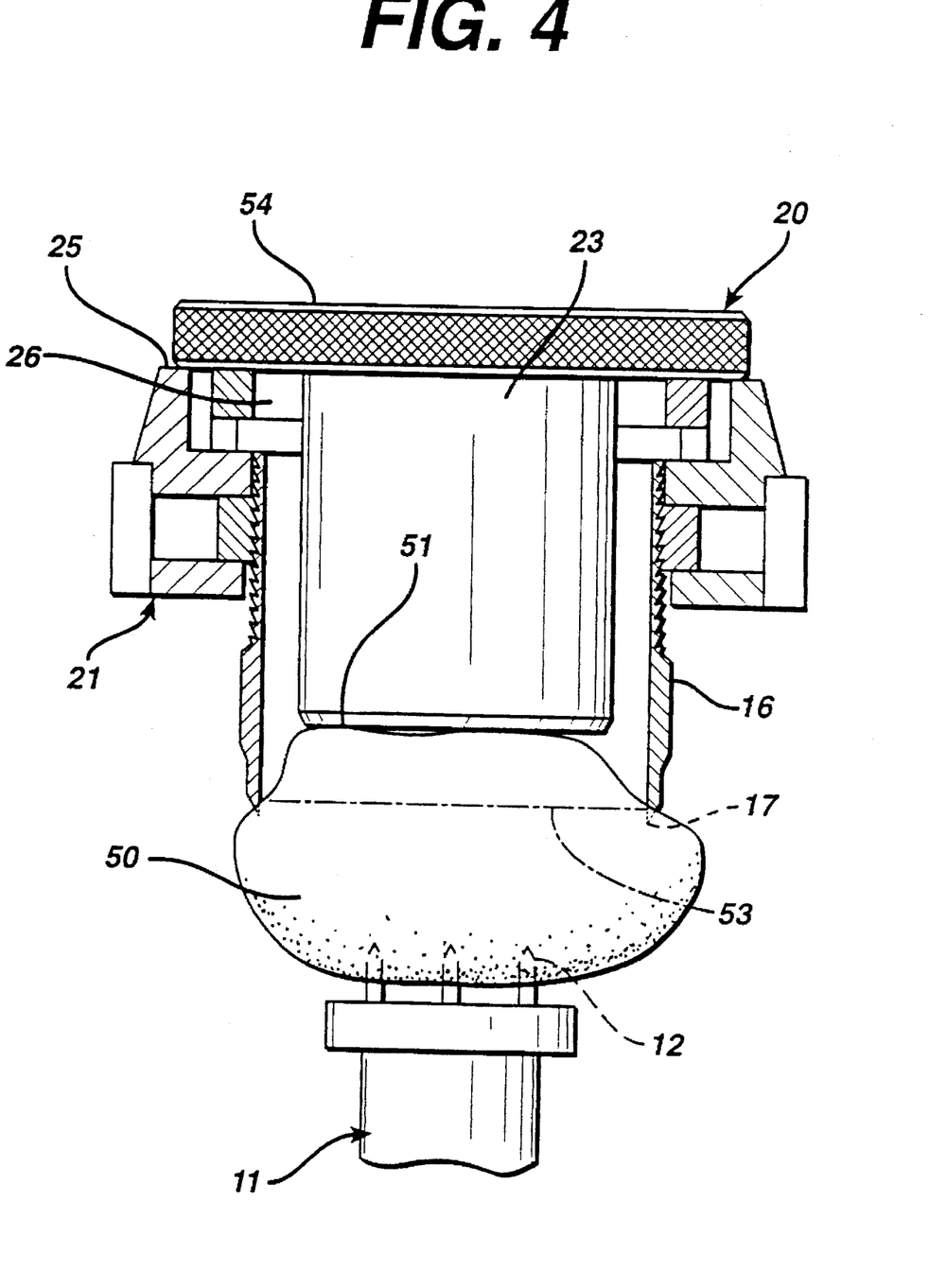
FIG. 4 illustrates a side cross-sectional view of the depth stop ring and depth stop plug of FIG. 2 inserted into the guide sleeve of FIG. 1.
Figure 5:
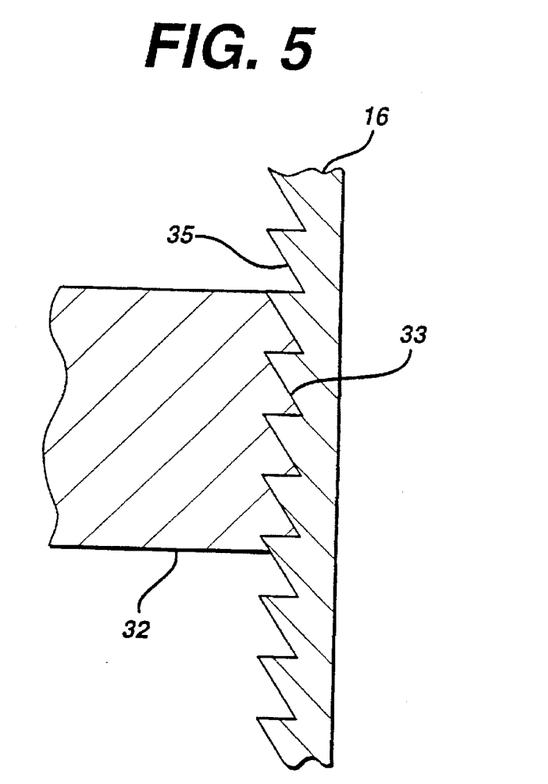
FIG. 5 illustrates an enlarged side cross-sectional view of the depth stop ring coupled to the guide sleeve of FIG. 4, illustrating lever and guide sleeve engaged by serrations.
Figure 7:
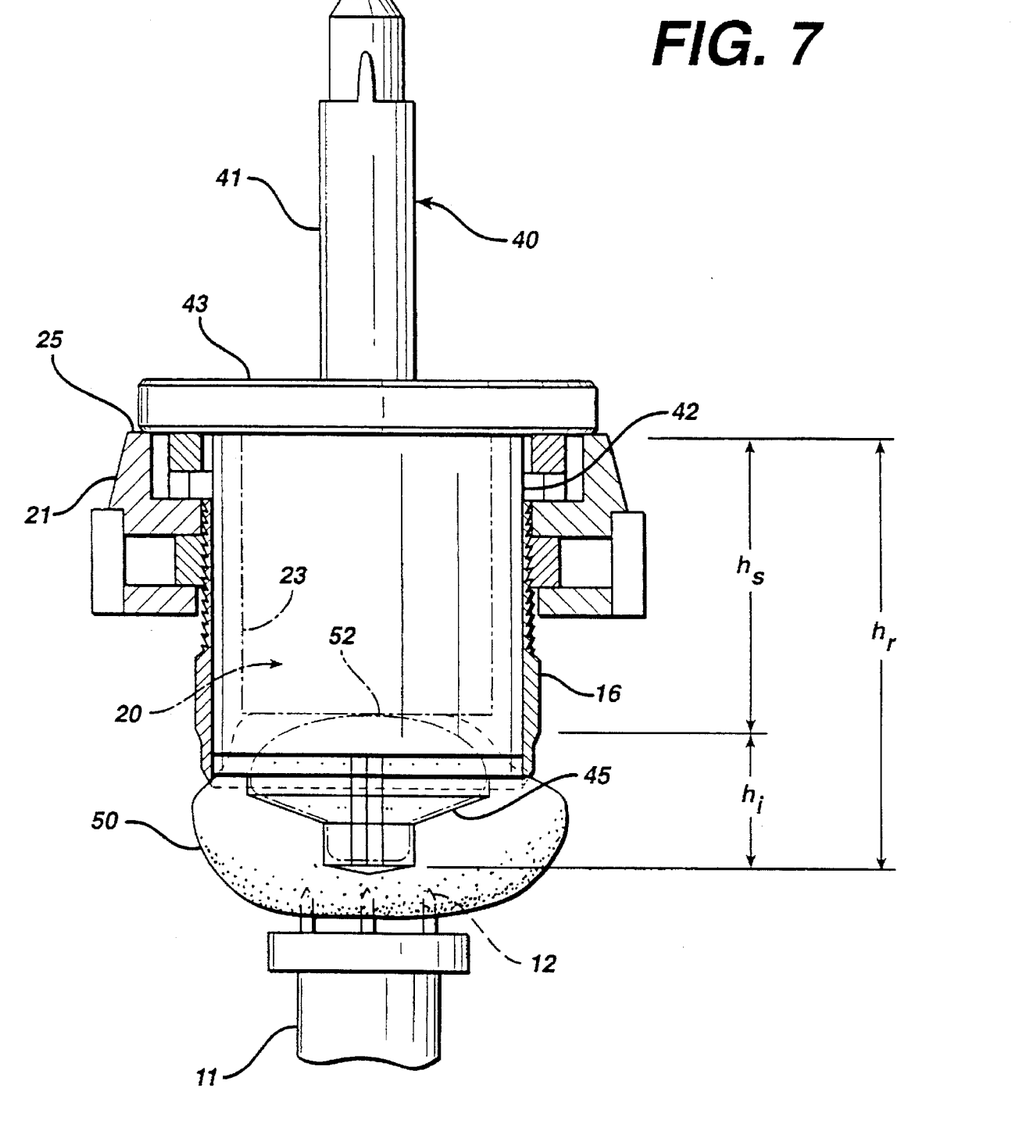
FIG. 7 illustrates the reaming step of the present invention utilizing the depth stop ring, guide sleeve, and reamer of FIGS. 1–6, and with the stop plug and a patellar prosthesis superimposed on the drawing.

FIGS. 4, 5 and 7 illustrate the median ridge referencing patella cutting system in use to prepare a patella 50 for implanting a patellar prosthesis 52. The surgical procedure for using the median ridge referencing patella instrument system includes the following steps:

First, the patella 50 is exposed according to known surgical techniques. The patella 50 is then sized and the appropriate implant size is selected. The reaming guide sleeve 16 is then clamped on the posterior side of the patella 50, between teeth 17 of guide sleeve 16 and pins 12 of the pedestal 11. The clamp 10 is firmly secured to the bone for the referencing and reaming steps. It may be noted here that various guide sleeves sizes may be used to accommodate the selected patellar prosthesis size.

In the next step the depth stop plug 20 is attached to the depth stop ring 21 by inserting the cylindrical portion 23 of the plug 20 through the opening 26 in the ring 21. The pins 24 under the head 22 of the plug 20 are inserted into the holes 27 of the ring 21. The plug 20 is locked on the ring 21 by turning it and thereby engaging the pins 24 in groove 28.

The assembled depth stop ring 21 and depth stop plug 20 are placed over the outer circumference of the guide sleeve 16. The cylinder 23 of the depth stop plug 20 extends inside the guide sleeve 16 until it reaches the patella 50. In doing this, the quick release locking levers 29 are squeezed at the tabs 30 to prevent the serrations 33 from engaging with the serrations 35 of the guide sleeve 16. The bottom of the plug 20 contacts the most prominent posterior point 51, which usually is the patellar median ridge. The depth stop ring 21 is locked in position on the guide sleeve 16 by releasing the tabs 30 of the levers 29. The 1 mm spacings between serrations 35 on the guide sleeve 16 allow accurate placement of the depth stop ring 21 within a 1 mm margin of error.

Figure 8:
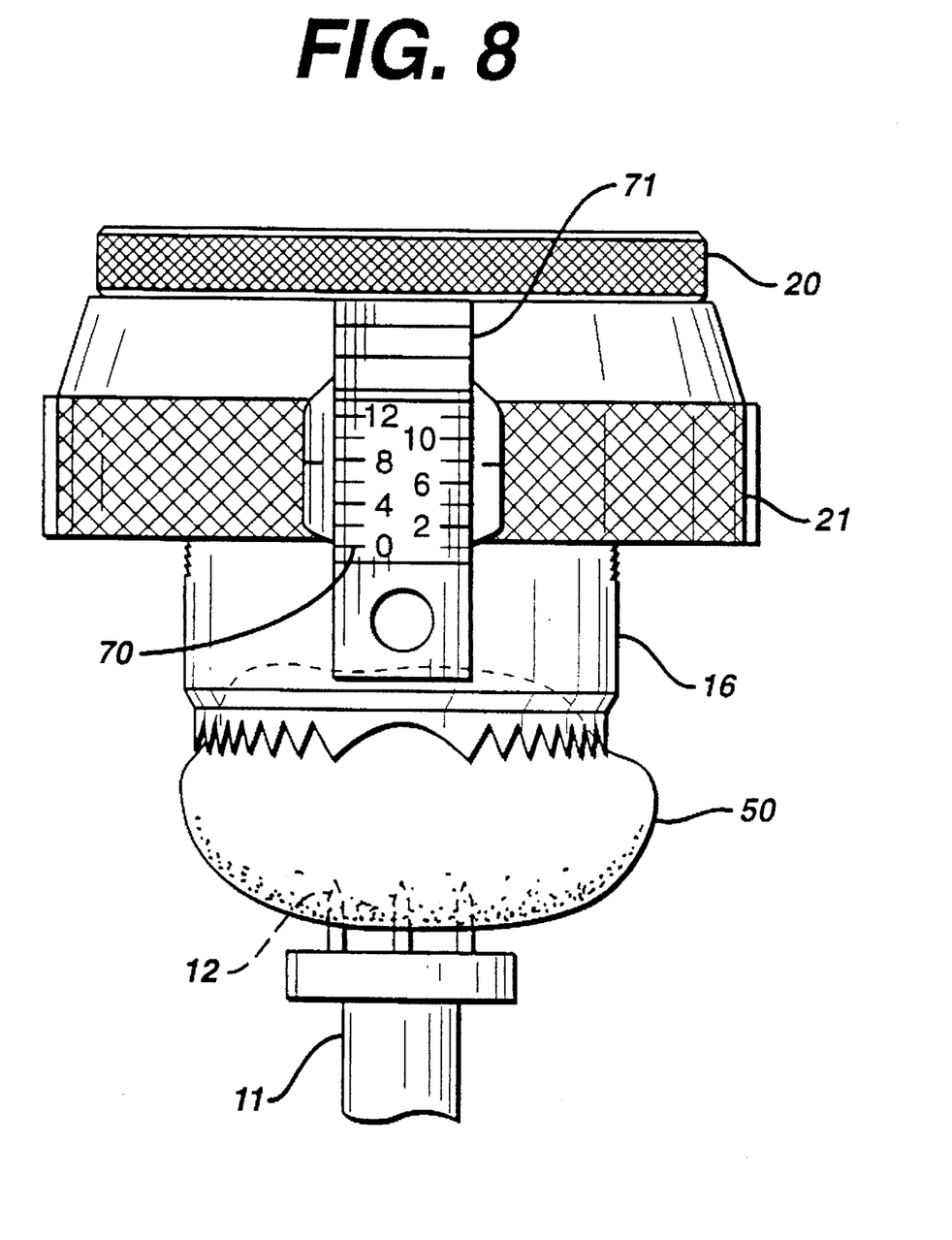
FIG. 8 illustrates a partial cross-section of the instrument of FIG. 7 including a depth stop ring with a metered height indicator.

The stop plug 20 may then be removed from the stop ring 21 by rotating the plug 20 so that pins 24 are aligned with holes 27 of the depth stop ring 21, and then separating the plug 20 from the ring 21. In one embodiment as illustrated in FIG. 8 the depth stop ring height can be checked, if desired, by viewing the position indicators 70 on the clamp ring tab 71. The height reading is a measurement between the most prominent posterior point 51 and the clamping teeth plane 53, (1 mm from the teeth 17 tips, to accommodate for protrusion of the teeth 17 into the patella 50 bone).

Once the depth stop ring 21 has been positioned, a reamer 40 designed for use with the guide sleeve 16 and the depth stop ring 21, may be used to ream the patella 50. The depth stop ring 21 in conjunction with the reamer 40 provides the appropriate reaming depth into the patella 50. The reamer 40 is inserted into the guide sleeve 16 and allowed to come to full speed before advancing into the patella surface. The reamer 40 is advanced until the reamer stop head 43 contacts the top 25 of the depth stop ring 21. This depth is designed to re-establish the patient's original patella thickness. The depth stop ring 21 may be raised or lowered to allow for lesser or deeper depth of reaming in the case of a thinner than usual patella or surgical revision situation. This is accomplished by squeezing the quick release locking levers 29 and moving the ring 21 while viewing the height indicator 70.

After the clamp 10 is removed, the patella prosthesis 52 may then be placed in the reamed hole of the patella 50. For purposes of illustration, a patellar prosthesis 52 is shown superimposed on FIG. 7 to illustrate its location when implanted. The depth of the prosthesis is illustrated as $h_i$. The stop plug 20 is also superimposed on FIG. 7 in the position where the stop plug 20 is hitting the most prominent point 53 of the original patella bone 50. Its height is shown as $h_s$. The reamer length from the stop head 43 the along the guide portion 42 to the cutting end 44 is illustrated as $h_r$. The height, $h_r$ is preset to be equal to the stop plug height $h_s$ plus the implant depth $h_i$.

Although the present invention is described with respect to specific embodiments, it is understood that numerous equivalents or modifications may be made without departing from the spirit and scope of the invention. The specific embodiment described herein is not intended to limit the claimed invention.

I claim:

1. A median ridge patella referencing system comprising:
    a patella clamp including a guide sleeve having a length and a lumen extending through the length;
    a referencing device comprising a coupling portion adapted to be coupled to the guide sleeve at a plurality of locations along the length of the guide sleeve, said coupling portion including an opening therethrough and a stop portion; a depth stop plug comprising a body portion and a head portion, said depth stop plug adapted to be removably coupled to the coupling portion when the body portion is extended through the opening in the coupling portion and the head portion abuts the stop portion of the coupling portion; and a reamer including a reamer stop, said reamer arranged to extend into the lumen of the guide sleeve until said reamer stop interacts with said stop portion of the coupling portion, whereby said reamer reams a patella clamped by the clamp.

2. The system of claim 1 wherein said guide sleeve includes an outer circumference and protrusions in the outer circumference; and wherein said coupling portion includes at least one engaging element arranged to couple the coupling element to a said protrusion of the guide sleeve.

3. The system of claim 2 wherein the said plurality of protrusions comprise serrations spaced at a preset distance from each other.

4. The system of claim 2 wherein said coupling portion includes a lever coupled to a said at least one engaging element, said lever arranged to move said protrusion from a first guide sleeve engaging position to a second free position.

5. The system of claim 4 wherein said lever is biased toward said first engaging position.

6. The system of claim 1 further comprising a median ridge height indicator located on said coupling portion.

7. A method of preparing a patella for implanting a patella prosthesis, the method comprising:

providing a clamp including a guide sleeve having a lumen for receiving a reamer and engagement elements coupled to the guide sleeve;

clamping a patella to be resurfaced, with the clamp;

providing a referencing device comprising a coupling portion and a depth stop plug removably coupled to said coupling portion, wherein the coupling portion includes a coupling element adapted to couple the coupling portion to the engagement elements and an opening for receiving a reamer, and wherein the depth stop plug is adapted to be inserted into the coupling portion and into the lumen of the guide sleeve;

inserting the depth stop plug into the coupling portion and the lumen of the guide sleeve until the depth stop plug reaches the patella;

coupling the coupling element of the coupling portion to a said engagement element of the guide sleeve;

removing the depth stop plug from the coupling portion and from the lumen of the guide sleeve;

providing a reamer having a reamer stop adapted to interact with the coupling portion when the reamer reaches a preset distance through the opening in the coupling portion;

inserting the reamer through the opening in the coupling portion and the lumen of the guide sleeve; and reaming the patella until the reamer stop interacts with the coupling portion to prevent the reamer from continuing, and until the reamer reaches the preset distance.

8. The method of claim 7 further comprising the step of manually positioning the coupling portion with respect to the guide sleeve prior to reaming the patella, to adjust the preset distance to an alternative distance.

* * * * *

UNITED STATES PATENT AND TRADEMARK OFFICE
CERTIFICATE OF CORRECTION

PATENT NO. : 5,658,291
DATED : August 19, 1997
INVENTOR(S) : Richard C. Techiera It is certified that error appears in the above-indentified patent and that said Letters Patent is hereby corrected as shown below:

On the title page, item [73],
    Change Assignee to: JOHNSON & JOHNSON PROFESSIONAL, INC.

Signed and Sealed this

Twenty-eighth Day of April, 1998

Attest:

BRUCE LEHMAN

*Attesting Officer*      *Commissioner of Patents and Trademarks*